United States Patent [19]

Kitazawa et al.

[11] Patent Number: 5,776,070
[45] Date of Patent: Jul. 7, 1998

[54] PULSE RATE COUNTER UTILIZING BODY MOVEMENT AMPTITUDE DETECTION

[75] Inventors: Kouji Kitazawa; Motomu Hayakawa, both of Suwa; Hiroshi Odagiri, Chiba, all of Japan

[73] Assignee: Seiko Epson Corporation, Tokyo, Japan

[21] Appl. No.: 602,650

[22] Filed: Feb. 16, 1996

[30] Foreign Application Priority Data

Feb. 20, 1995 [JP] Japan ................................ 7-031018
Feb. 9, 1996 [JP] Japan ................................ 8-024510

[51] Int. Cl.$^6$ .............................................. A61B 5/0205
[52] U.S. Cl. ................................... 600/483; 600/503
[58] Field of Search .............................. 128/670, 687, 128/689, 690, 700; 600/483, 500, 502, 503, 513

[56] References Cited

U.S. PATENT DOCUMENTS 4,239,048 12/1980 Steuer ................................ 128/690
5,025,791 6/1991 Niwa ................................ 128/670
5,475,725 12/1995 Nakamura ........................ 128/689
5,515,858 5/1996 Myllymaki ........................ 128/670

FOREIGN PATENT DOCUMENTS 60-259239 12/1985 Japan.

*Primary Examiner*—William E. Kamm
*Attorney, Agent, or Firm*—Mark P. Watson

[57] ABSTRACT

A pulse rate counter that can accurately measure pulse rate regardless of whether the user is resting or exercising is disclosed. In the pulse rate counter, a pulse wave component extraction means extracts pulse wave components based on the frequency analysis results of a first calculation means and a second calculation means. During this process, an extraction method switching means determines whether the user is resting or exercising based on the amplitude level of the signal output of a body movement signal conversion means, the level (power) of the frequency spectrum of the output signal of the second calculation means, or the degree of variation in the level. If the user is determined to be resting, the extraction method switching means causes the pulse wave component extraction means to extract the pulse wave components based on the frequency analysis result of the first calculation means.

19 Claims, 13 Drawing Sheets

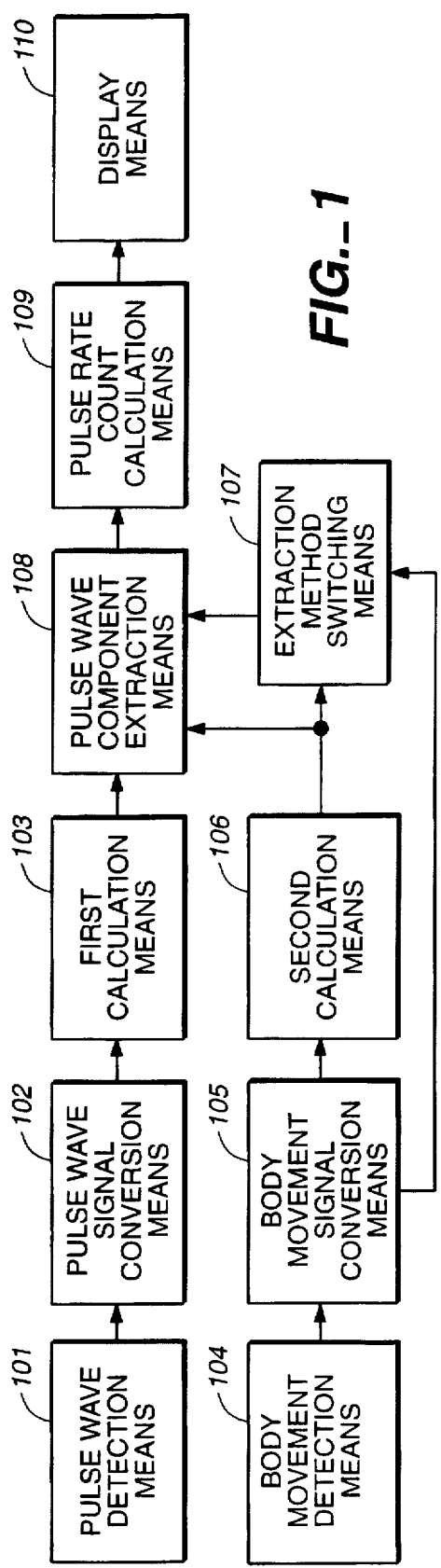
FIG._1
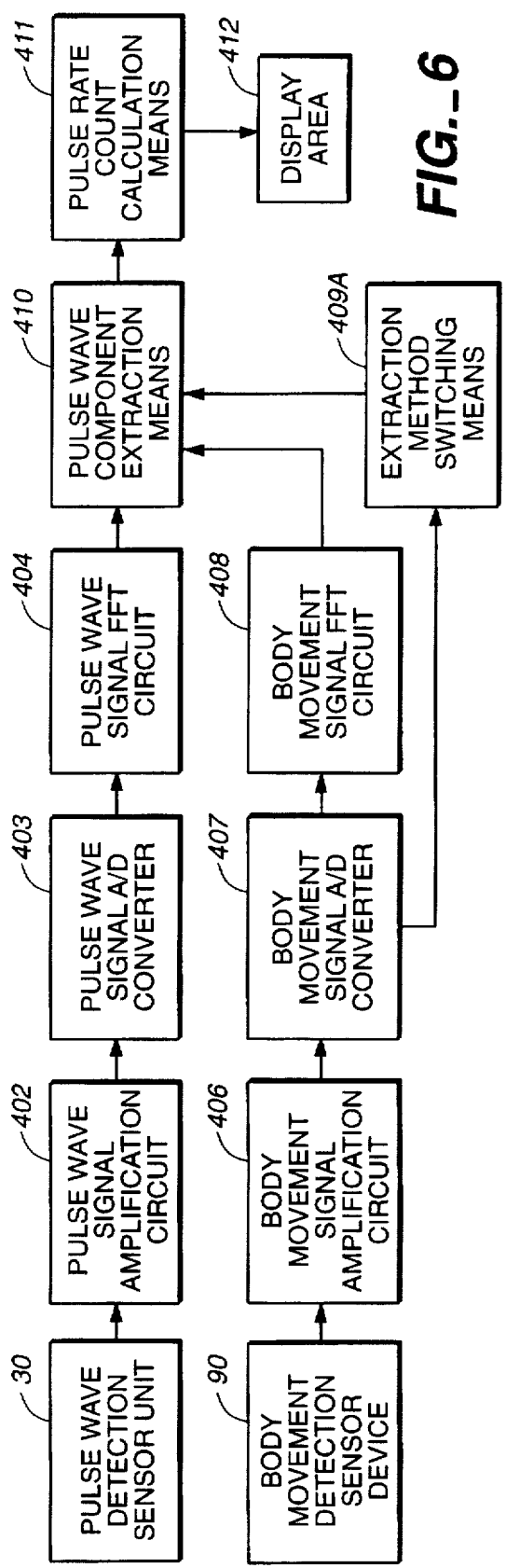
FIG._6

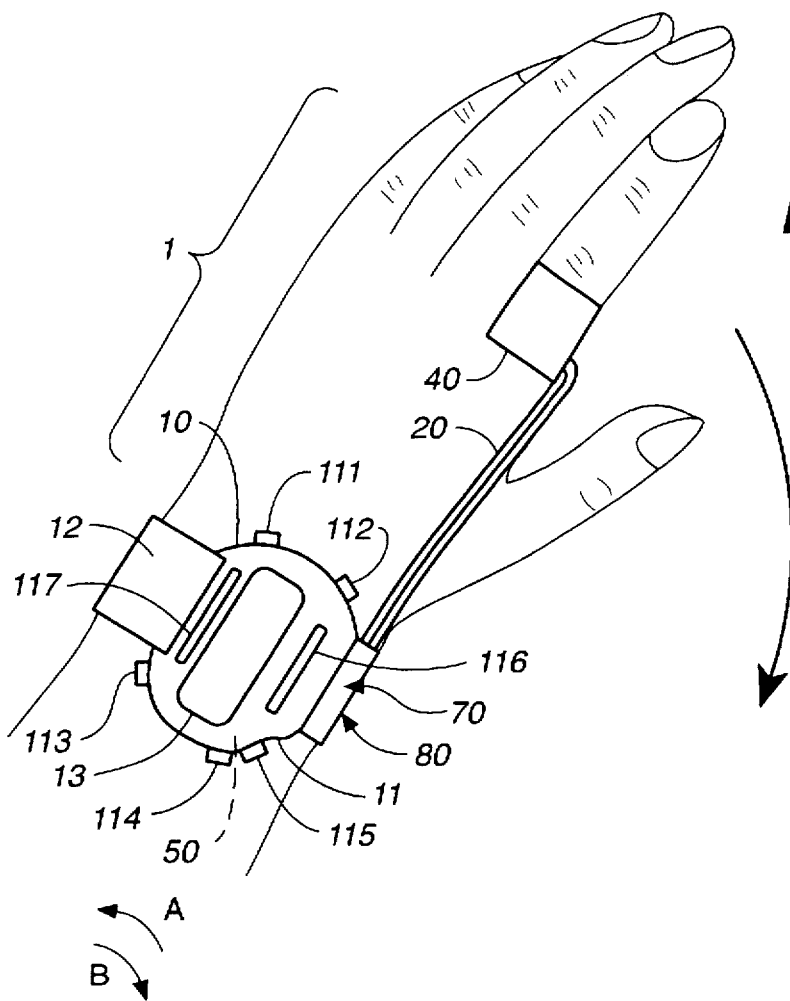
FIG._2A
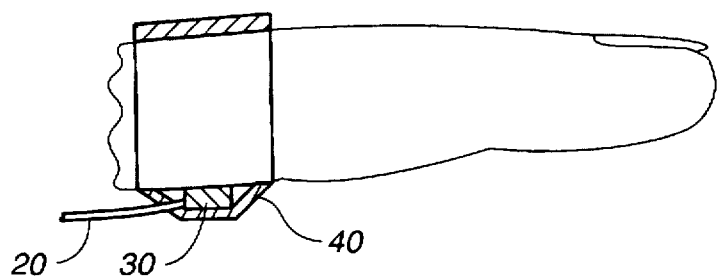
FIG._2B

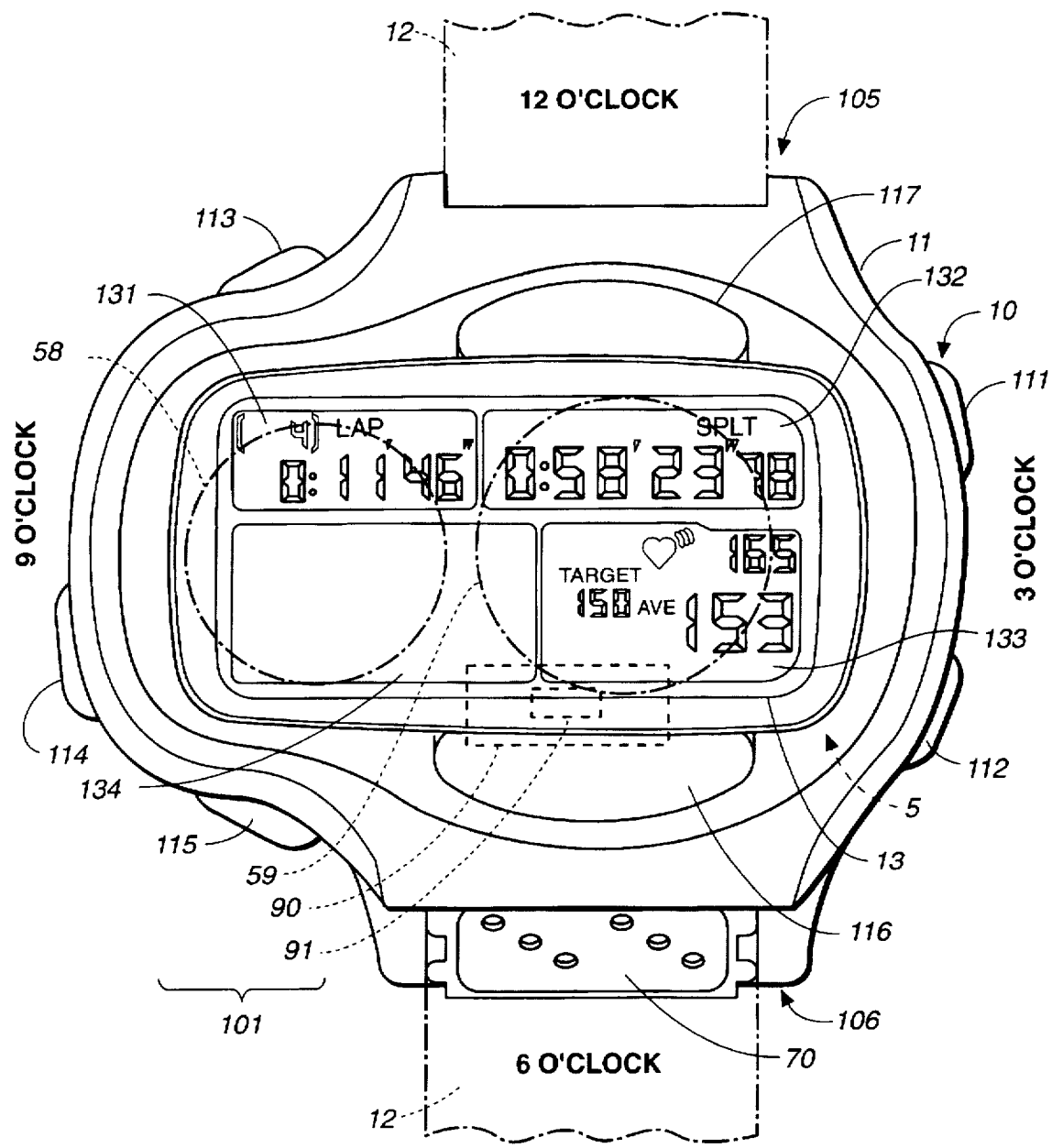
FIG._3

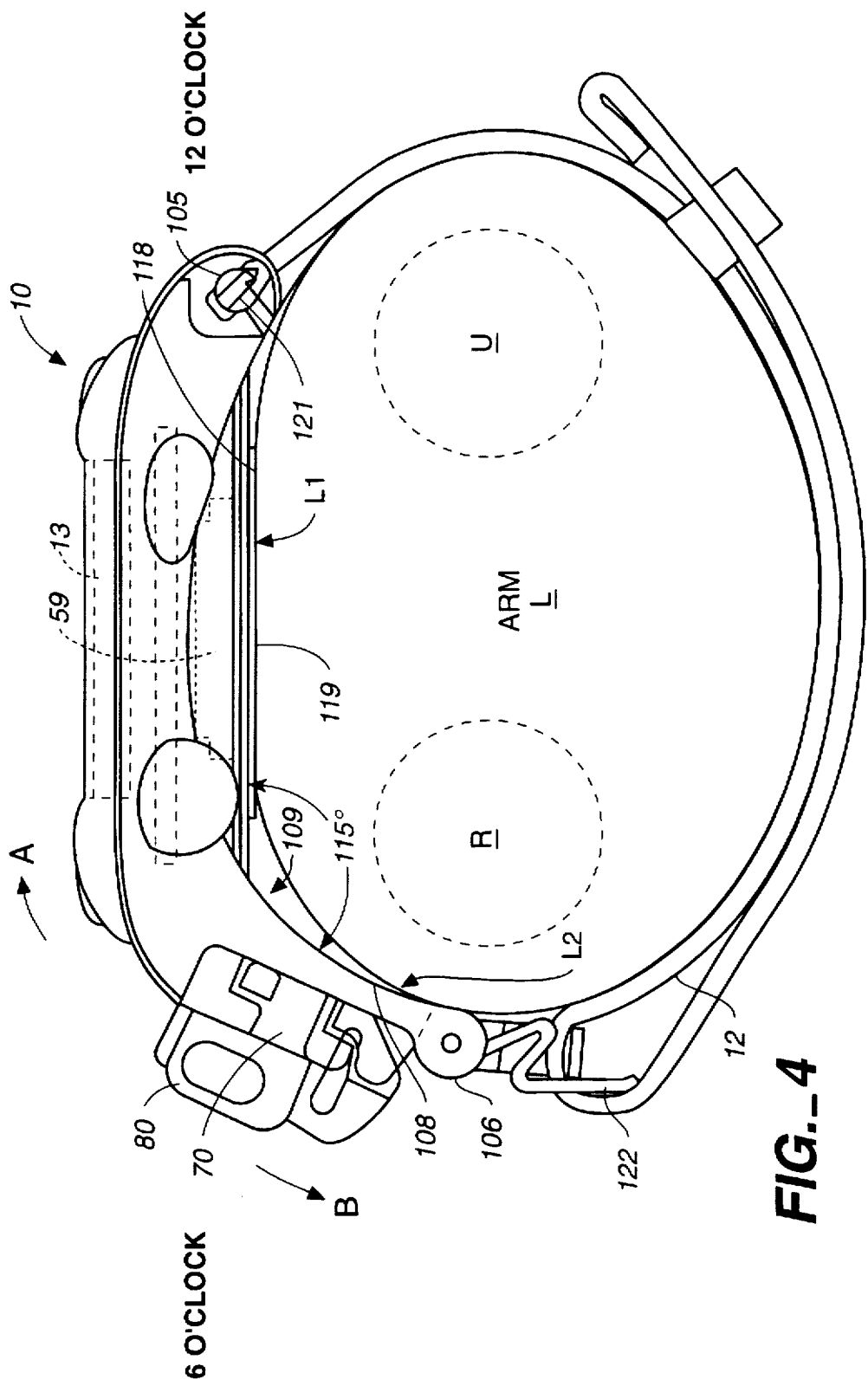
FIG._4

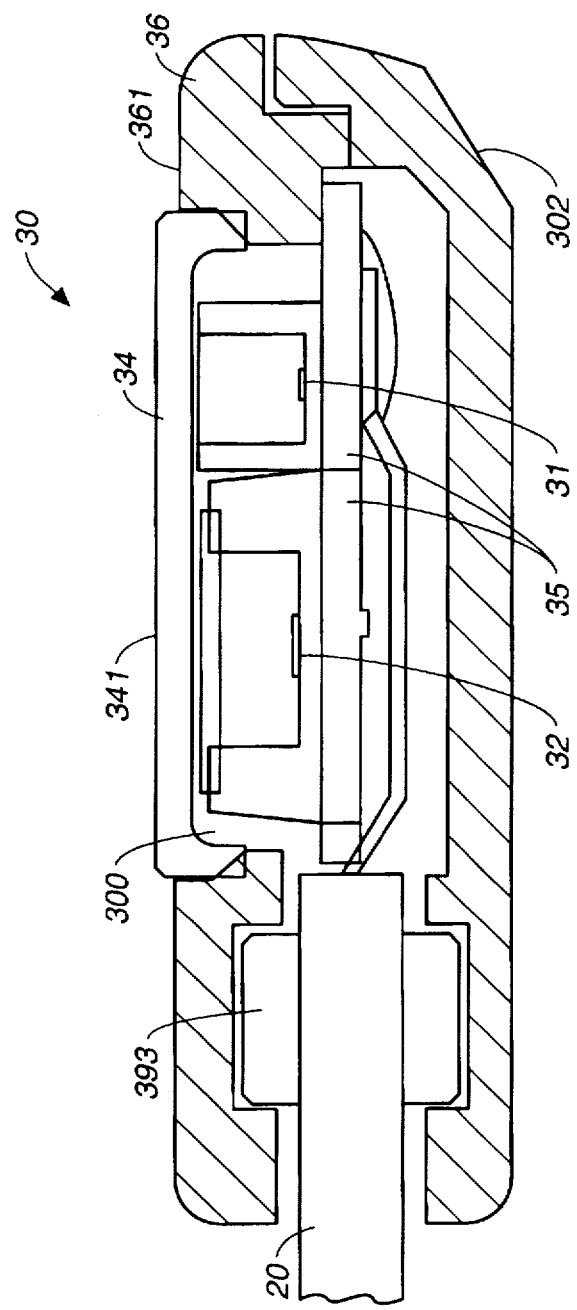
FIG._5

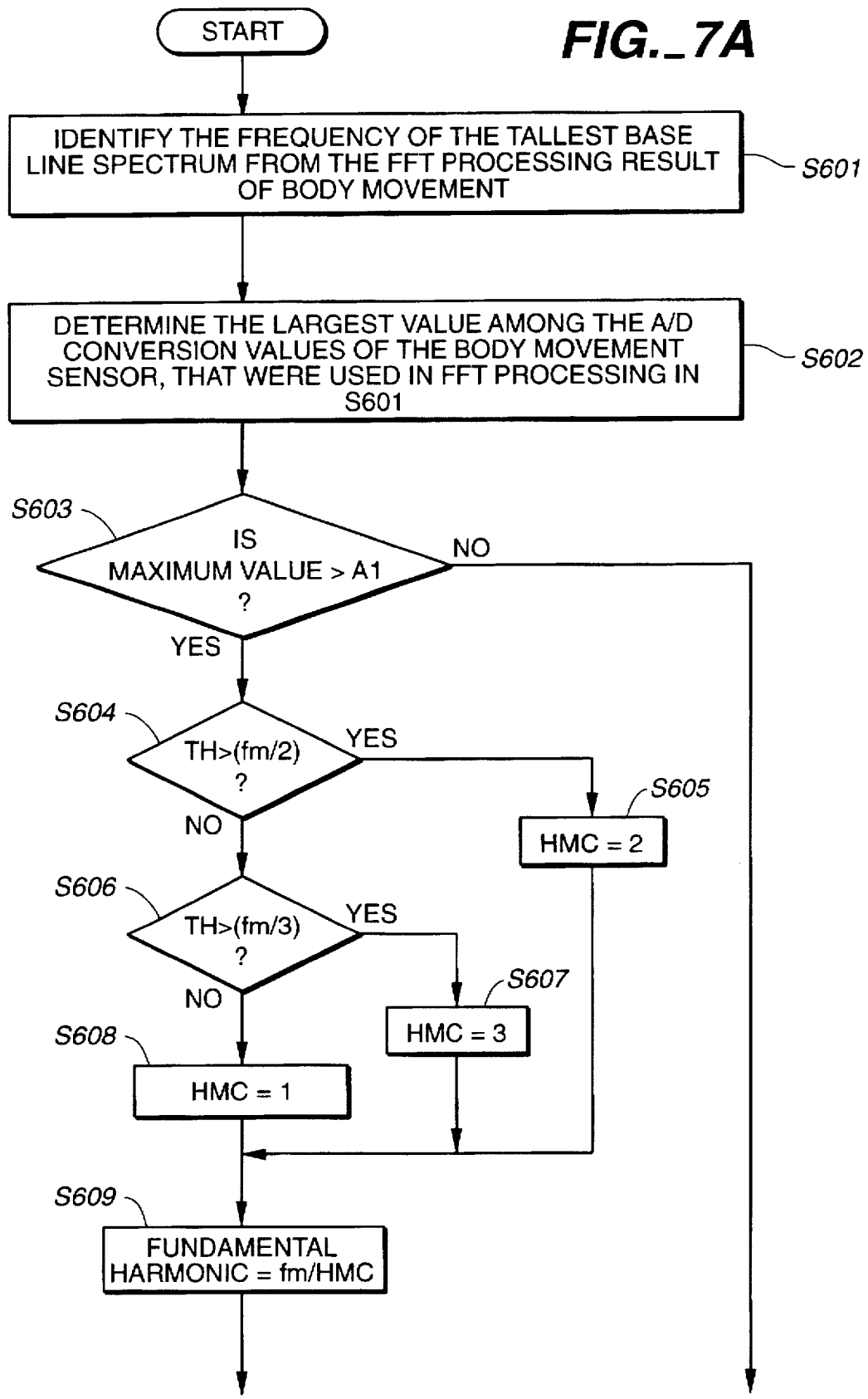
FIG._7A

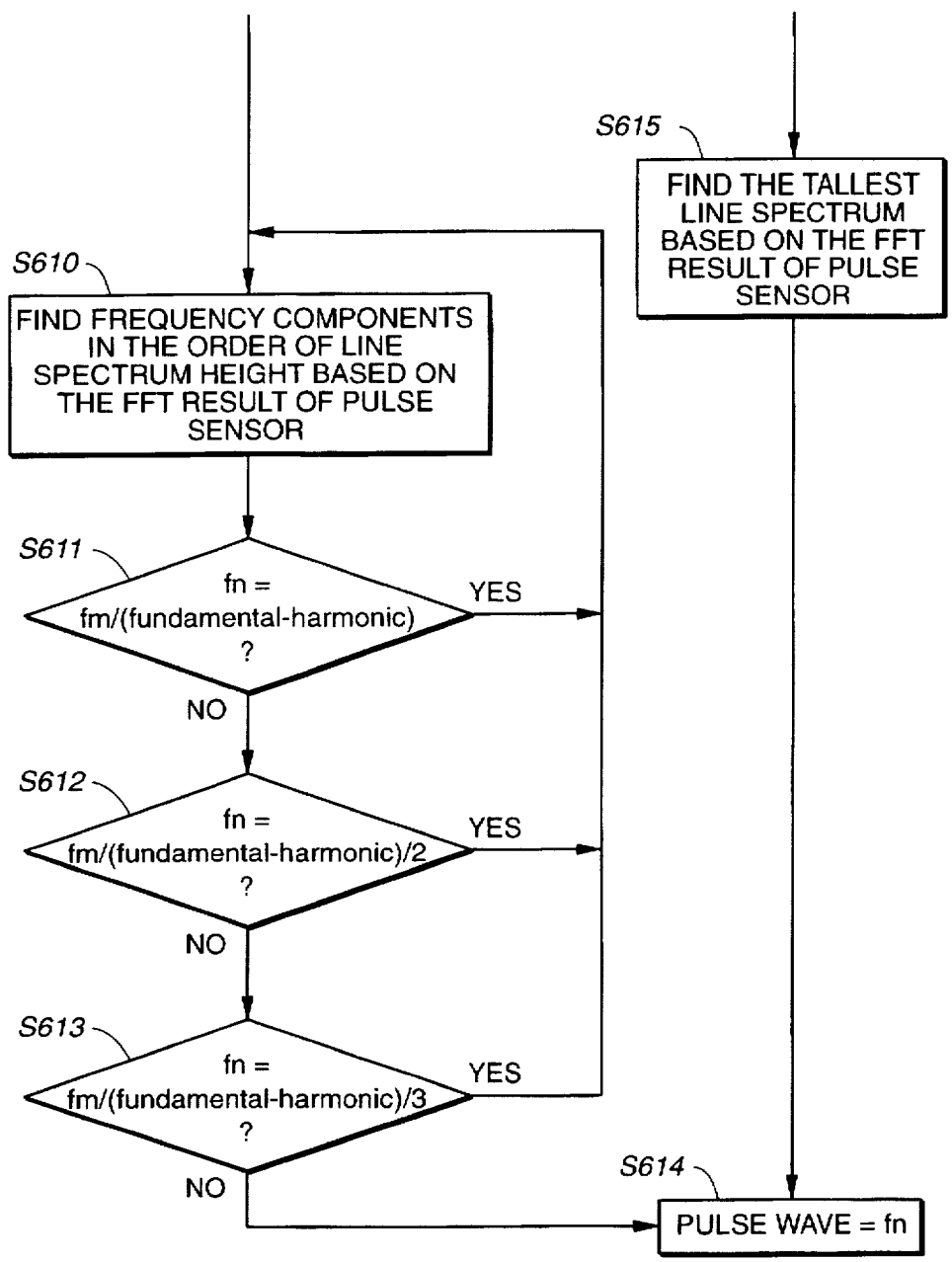
FIG._7B
FIG._7A
FIG._7B FIG._7

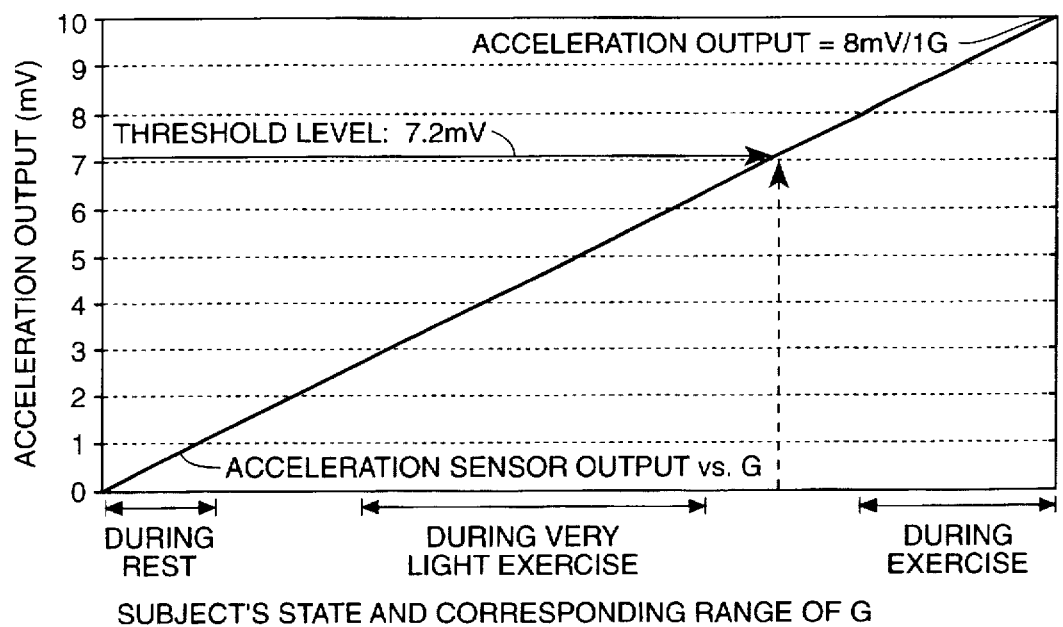
FIG._8
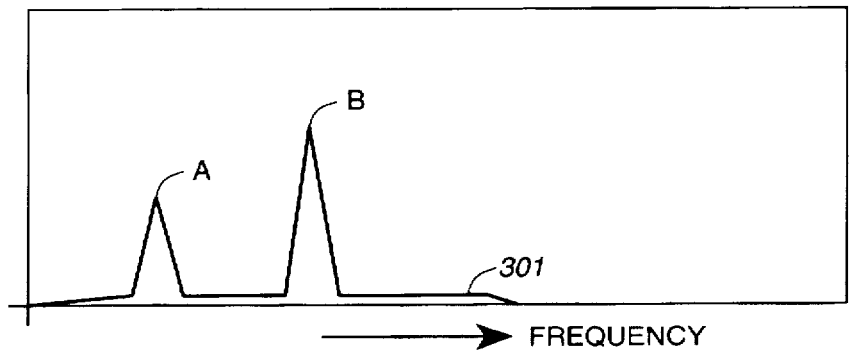
FIG._13A
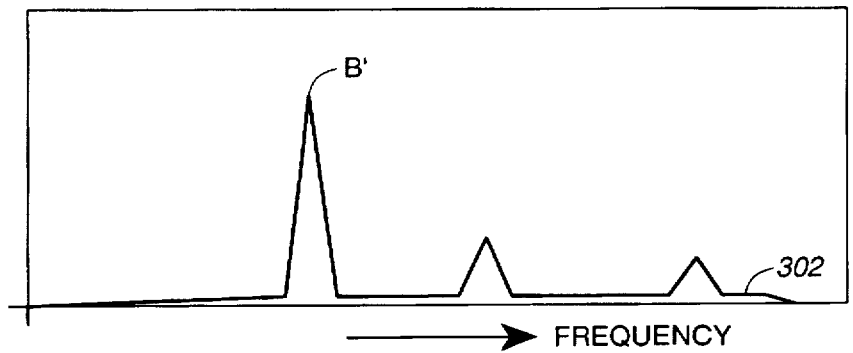
FIG._13B

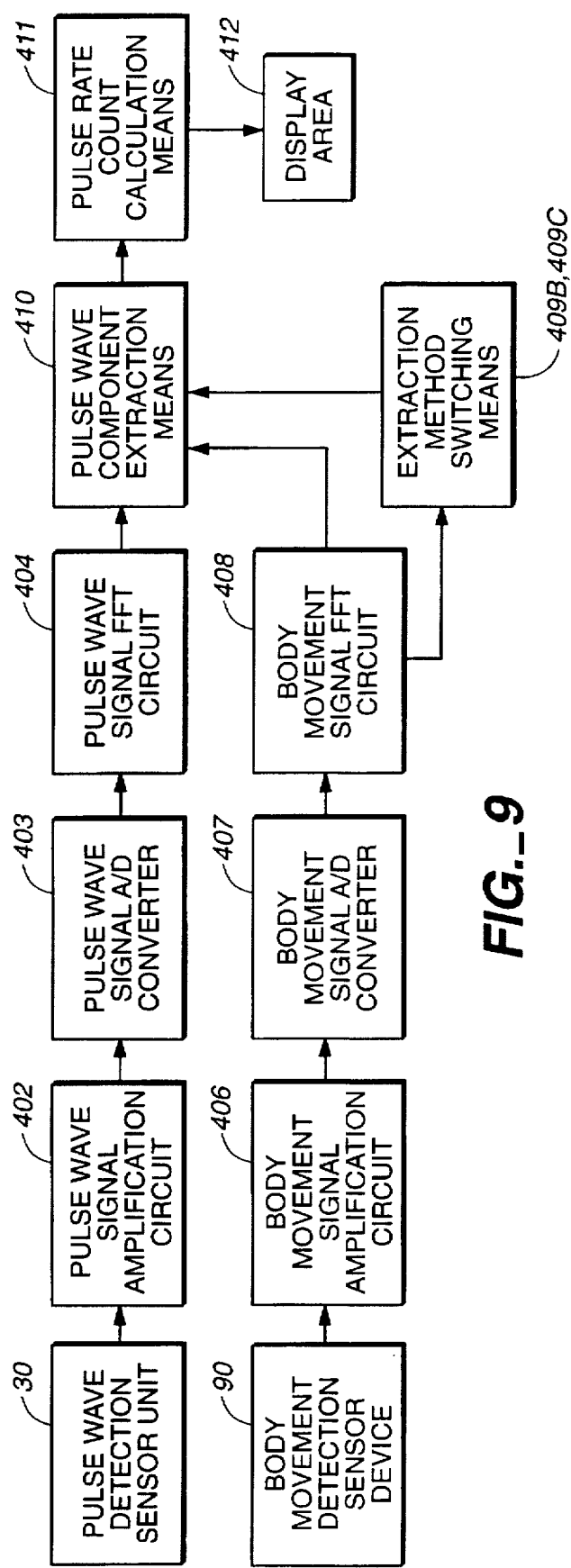
FIG._9
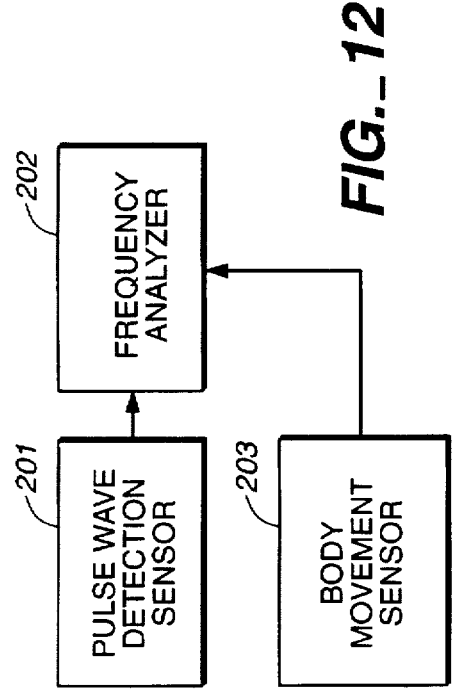
FIG._12

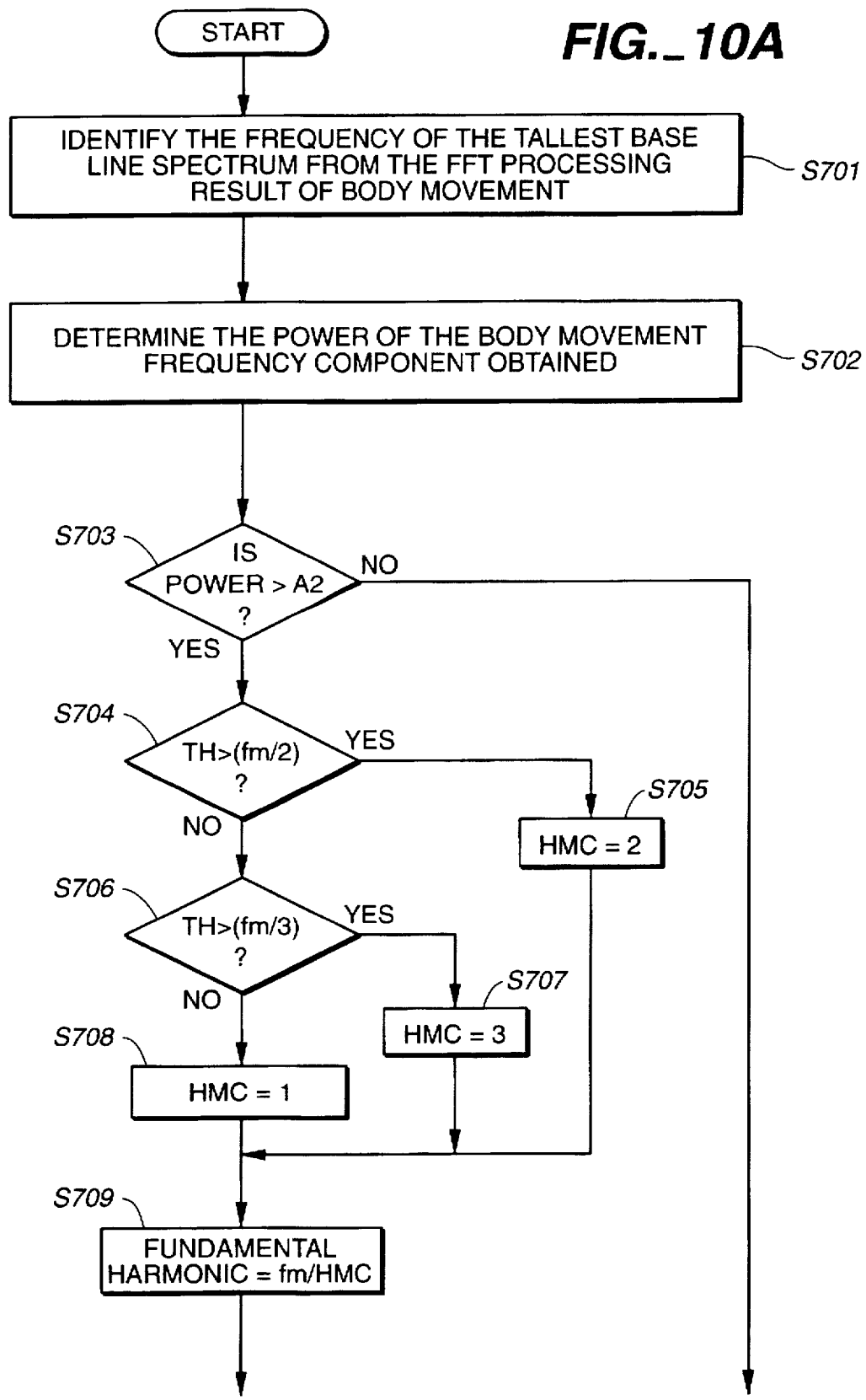
FIG._10A

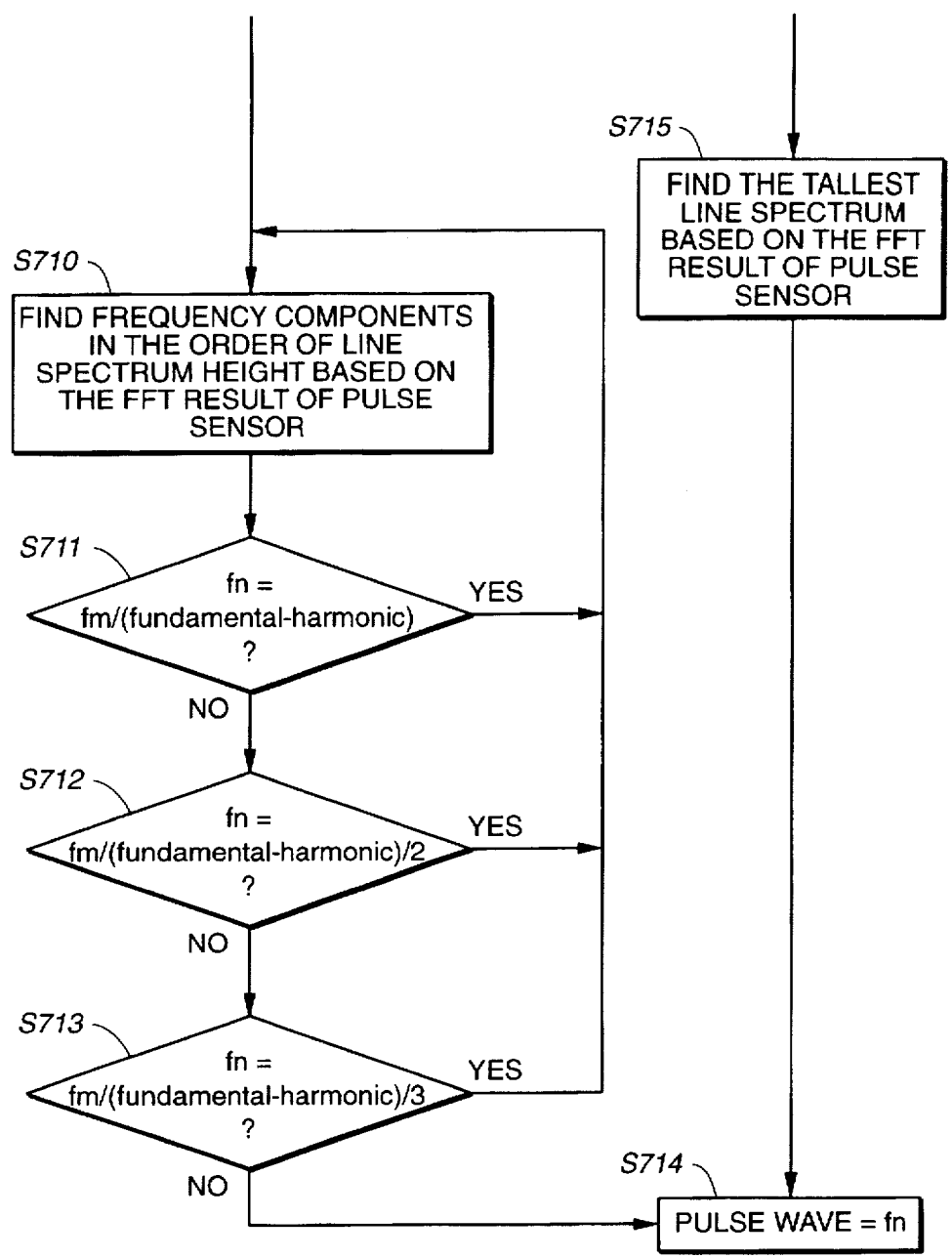
FIG._10B
FIG._10

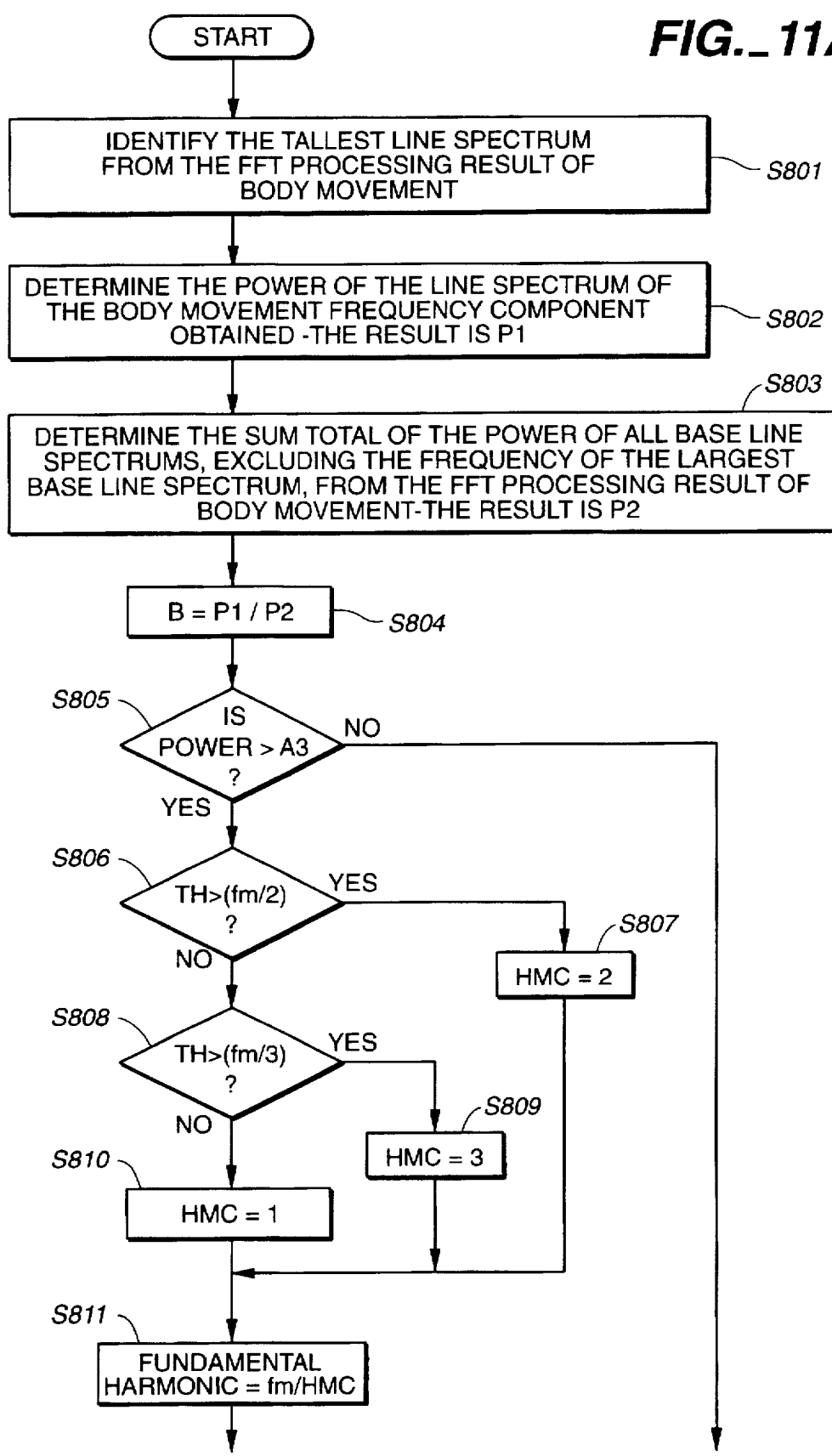
FIG._11A

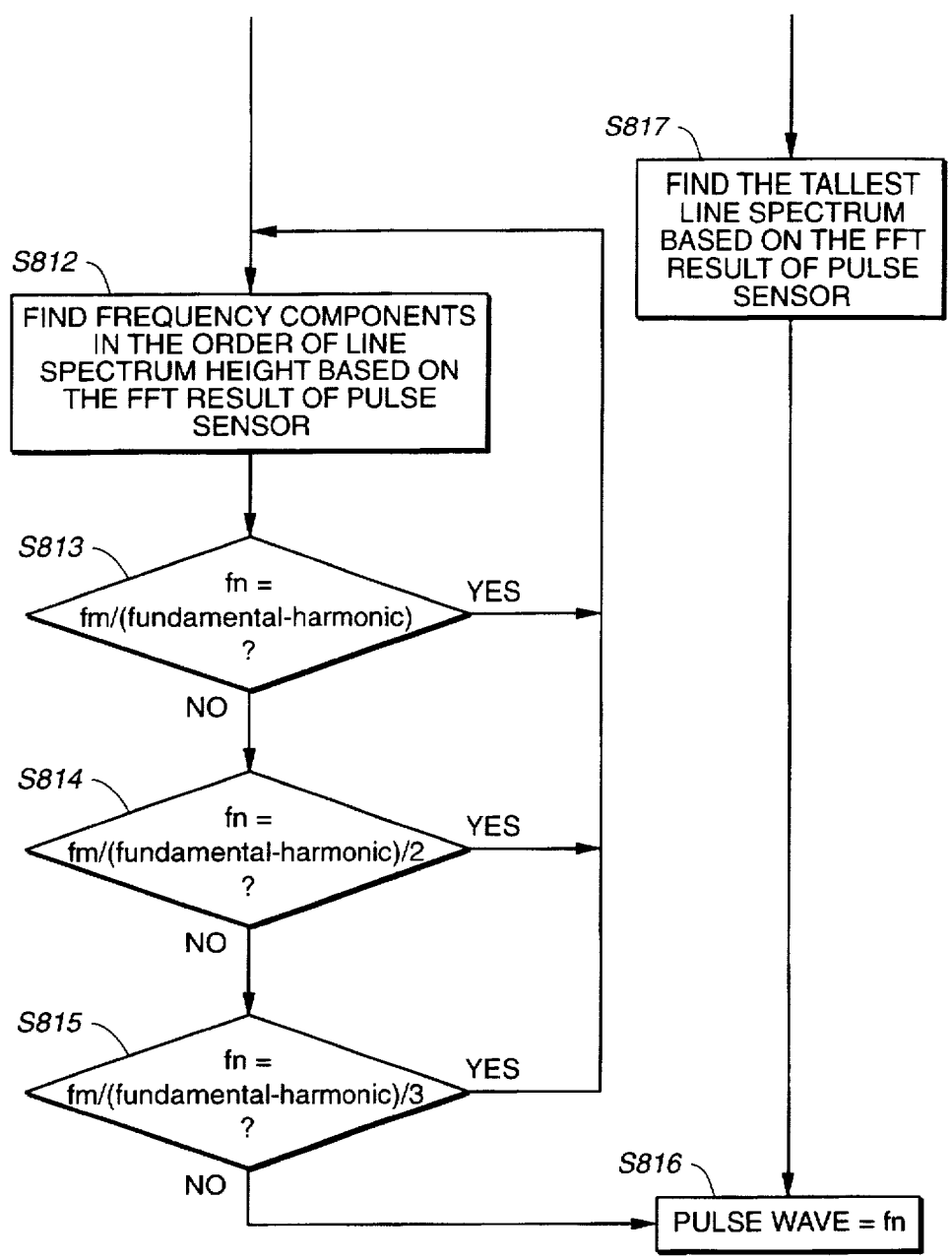
FIG._11B
FIG._11A
FIG._11B    FIG._11

5,776,070

1

PULSE RATE COUNTER UTILIZING BODY MOVEMENT AMPTITUDE DETECTION

BACKGROUND OF THE INVENTION

1. Field of the Invention

The invention relates to a pulse rate counter used by a person for managing exercise and health. In particular, the invention relates to the signal-processing technology for measuring pulse rates with a high degree of accuracy both during rest and exercise.

2. Description of the Related Art

Since the ability to measure the pulse rate during marathon or jogging enables the user to manage the degree of exercise to avoid dangerous situations, portable pulse rate counters that can be worn on the arm have been suggested. Such a portable pulse rate counter uses an optical sensor for measuring the pulse wave signal, and determines the pulse rate by extracting the signal that corresponds to the pulse rate from this pulse wave signal. However, because the pulse wave signal measured during jogging also contains a signal component that is generated by the body movement, the signal that corresponds to the pulse cannot be extracted as is.

Therefore, as shown in FIG. 12, in the pulse rate counter disclosed in Japanese patent application No. 60-259239, body movement detection sensor 203, as well as pulse wave detection sensor 201, are provided for a single pulse rate counter. The frequency components of the signals obtained from both of these sensors are analyzed by frequency analyzer 202. According to frequency analyzer 202, as shown in FIGS. 13A and 13B, the pulse wave signal detected by pulse wave detection sensor 201 is converted to the spectrum indicated by waveform 301; and the body movement signal detected by body movement detection sensor 203 is converted to the spectrum indicated by waveform 302. Since waveform 302 is the result of the frequency analysis of the signal detected by body movement detection sensor 203, peak B' which expresses its fundamental harmonic element indicates the fundamental frequency of body's vibration. Therefore, when the frequency of peak B' matches that of peak B in waveform 301, peak B in waveform 301 can be determined to be the waveform caused by the body's vibration, and thus the peak that remains when peak B is eliminated from waveform 301, i.e., peak A, can be judged to be the waveform that corresponds to the pulse.

However, with conventional pulse rate counters, the user must compare the frequency analysis result of the signal detected by pulse wave detection sensor 201 with the frequency analysis result of the signal detected by body movement detection sensor 203; and to obtain the pulse rate during exercise, the user must subtract the frequency analysis result of the signal detected by body movement detection sensor 203 from the frequency analysis result of the signal detected by pulse wave detection sensor 201. In contrast, to obtain the pulse rate while the user is at rest, the user must use the frequency analysis result of the signal detected by pulse wave detection sensor 201 as is. Therefore, the pulse rate counter must be manually operated each time, making it user-unfriendly.

The need exists for automating this process by eliminating such manual operations. However, since a conventional pulse rate counter is not provided with a means for judging whether the user is resting or exercising, it must perform the same calculation regardless of whether the user is resting or exercising. As a result, although the pulse rate during exercise can be obtained by subtracting the frequency analysis result of the signal detected by body movement detection

2 sensor 203 from the frequency analysis result of the signal detected by pulse wave detection sensor 201, correct pulse rate during rest cannot be obtained due to the effect of noise. In other words, although the signal detected by body movement detection sensor during rest should only contain noise elements, if the frequency of this noise element coincides with the frequency corresponding to the pulse rate, the following will take place. When the frequency analysis result of the signal detected by body movement detection sensor 203 is subtracted from the frequency analysis result of the signal detected by pulse wave detection sensor 201, the frequency corresponding to the pulse rate will be subtracted from the frequency analysis result of the signal detected by pulse wave detection sensor 201. Consequently, the signal detected by pulse wave detection sensor 201 loses the frequency corresponding to the pulse rate, and thus pulse rate cannot be accurately measured.

Therefore, it is an object of the present invention to overcome the aforementioned problems.

SUMMARY OF THE INVENTION

In order to solve the above-mentioned problem, the invention provides a pulse rate counter that can accurately measure pulse rate regardless of whether the user is resting or exercising.

The pulse rate counter according to the first embodiment of the invention comprises a first calculation means for analyzing the frequency of the pulse signal of a body detected by a pulse wave detection sensor, a second calculation means for analyzing the frequency of a body movement signal detected by a body movement detection sensor, a pulse wave component extraction means for extracting pulse frequency components from the frequency analysis results of the first and second calculation means, an extraction method switching means for switching the extraction method of the pulse wave component extraction means to operate in a predetermined method according to the amplitude level of the body movement signal, and a pulse rate calculation means for converting the pulse frequency components extracted by the pulse wave component extraction means to a pulse rate for display.

The pulse rate counter according to the second embodiment of the invention comprises a first calculation means for analyzing the frequency of the pulse signal of a body detected by a pulse wave detection sensor, a second calculation mans for analyzing the frequency of a body movement signal detected by a body movement detection sensor, a pulse wave component extraction means for extracting pulse frequency components from the frequency analysis results of the first and second calculation means, an extraction method switching means for switching the extraction method of the pulse wave component extraction means to operate in a predetermined method according to the frequency spectrum level of the frequency analysis result obtained by the second calculation means, and a pulse rate calculation means for converting the pulse frequency components extracted by the pulse wave component extraction means to a pulse rate for display.

The pulse rate counter according to this second embodiment can be configured such that the extraction method switching means switches the extraction method of the pulse wave component extraction means to operate in a predetermined method according to the relative comparison result of the multiple frequency spectrum levels obtained by the second calculation means.

In the invention, the pulse wave component extraction means is operable in two extraction methods comprising, for example, a first extraction method for extracting pulse frequency components based on the frequency analysis result of the first calculation means, and a second extraction method for extracting pulse frequency components based on the frequency analysis results of the first and second calculation means, wherein one of these methods is selected by an extraction method switching means.

Other objects and attainments together with a fuller understanding of the invention will become apparent and appreciated by referring to the following description and claims taken in conjunction with the accompanying drawings.

BRIEF DESCRIPTION OF THE DRAWINGS

In the drawings wherein like reference symbols refer to like parts:

FIG. 1 is a functional block diagram showing a representative configuration of the pulse rate counter of the invention;

FIGS. 2A and 2B show the overall configuration of the wristwatch type pulse rate counter related to a working example of the invention and how the counter is used;

FIG. 3 is a top view of the device main body of the wristwatch type pulse rate counter shown in FIG. 2;

FIG. 4 is a diagram of the device main body of the wristwatch type pulse rate counter shown in FIG. 2, viewed from the 3 o'clock direction of the watch;

FIG. 5 is a cross-section of the sensor unit used in the wristwatch type pulse rate counter shown in FIG. 2;

FIG. 6 is a functional block diagram of the pulse rate counter related to Working example 1 of the invention;

FIG. 7 is comprised of FIGS. 7A and 7B; FIG. 7A and 7B are a flow chart showing an overview of the operation of the extraction method switching means in the pulse rate counter related to Working example 1 of the invention;

FIG. 8 is a graph showing the relationship between the state (acceleration G) of the user who is wearing the pulse rate counter related to Working example 1 of the invention and the output of the acceleration sensor which is used as the threshold for determining whether the user is resting or exercising;

FIG. 9 is a functional block diagram of the pulse rate counter related to Working examples 2 and 3 of the invention;

FIG. 10 is comprised of FIGS. 10A and 10B; FIGS. 10 and 10B are a flow chart showing an overview of the operation of the extraction method switching means in the pulse rate counter related to Working example 2 of the invention;

FIG. 11 is comprised of FIGS. 11A and 11B; FIGS. 11A and 11B are a flow chart showing an overview of the operation of the extraction method switching means in the pulse rate counter related to Working example 3 of the invention;

FIG. 12 is a functional block diagram showing the configuration of a conventional pulse rate counter; and FIGS. 13A and 13B show an overview of pulse wave extraction.

Description of the Preferred Embodiments

DESCRIPTION OF THE PREFERRED EMBODIMENTS

FIG. 1 is a functional block diagram showing an example of a representative configuration of the pulse rate counter of the invention.

In this figure, pulse wave detection means 101 is provided with a pulse wave detection sensor for detecting pulse waves from a human or an animal. The analog signal (pulse wave signal) detected by pulse wave detection means 101 is first converted to a digital signal by pulse wave signal conversion means 102 and is then output to first calculation means 103. First calculation means 103 is provided with a frequency analysis means for pulse wave signals, and analyzes the frequency of the digital signal that is output by pulse wave signal conversion means 102, and then outputs the result to pulse wave component extraction means 108.

On the other hand, body movement detection means 104 is provided with a body movement detection sensor for detecting the movement of the human or animal for whom pulse rate is being measured. The analog signal detected by body movement detection means 104 is converted to a digital signal by body movement signal conversion means 105, and is then output to second calculation means 106. Second calculation means 106 is provided with a frequency analysis means for body movement signals, and analyzes the frequency of the digital signal that is output by body movement signal conversion means 105, and then outputs the result to pulse wave component extraction means 108.

Pulse wave component extraction means 108 extracts pulse wave frequency components from the signals output by first calculation means 103 and second calculation means 106. Here, extraction method switching means 107 is configured such that it selects between two extraction methods, i.e., the first extraction method which extracts pulse frequency from the frequency analysis result (corresponding to spectrum (a) in FIG. 13) of first calculation means 103 only, or the second extraction method which extracts pulse frequency from both the frequency analysis result of first calculation means 103 and the frequency analysis result (corresponding to spectrum (b) in FIG. 13) of second calculation means 106.

Pulse rate calculation means 109 converts the pulse frequency component extracted by pulse wave component extraction means 108 to a pulse rate. Display means 110 displays the pulse rate obtained by pulse rate calculation means 109.

The pulse rate counter of the invention is provided with extraction method switching means 107. This extraction method switching means 107 is configured such that it automatically determines whether the user is resting or exercising based on the output signal of body movement signal conversion means 105 or second calculation means 106, and based on this result, selects an appropriate pulse wave component extraction method (first or second extraction method) to be used by pulse wave component extraction means 108.

In other words, extraction method switching means 107 is configured such that it switches the pulse wave component extraction method between exercise and rest periods by automatically detecting the differences in body movement signal levels and frequency components that normally exist between exercise and rest periods.

To detect such differences, the inventor has developed simple but superior methods listed below and has arrived at this invention by skillfully utilizing these methods for pulse wave component extraction.

(1) Determination method that uses the amplitude level of body movement signal (2) Determination method that uses the frequency spectrum level of body movement signal Note that the second method, (2) Determination method that uses the frequency spectrum level of body movement signal, can be either (a) Determination method that uses maximum spectrum level (power) or (b) Determination method that uses spectrum level (power) variation (relative comparison result of individual spectrum levels), which is an applied form of (a).

Pulse rate counters related working examples in which the above determination methods are used during rest and exercise are explained below. Working example 1 uses "(1) Determination method that uses the amplitude level of body movement signal." Working example 2 uses "(2-a) Determination method that uses frequency spectrum level of body movement signal (maximum spectrum level (power))," and Working example 3 uses "(2-b) Determination method that uses frequency spectrum level (spectrum level (power) variation).

WORKING EXAMPLE 1

OVERALL CONFIGURATION:

FIGS. 2A and 2B show the configuration of the pulse rate counter of this working example.

In FIGS. 2A and 2B, pulse rate counter 1 (portable pulse wave counter) of this example primarily comprises device main body 10 having a wristwatch structure, cable 20 connected to this device main body 10, and pulse wave detection sensor unit 30 (pulse wave signal detection sensor) installed on the tip of this cable 20. The tip of cable 20 is provided with connector piece 80 which is detachably attached to connector area 70 provided on the 6 o'clock side of device main body 10. Wristband 12, which is wrapped around the wrist from the 12 o'clock direction of the wristwatch and fastened in the 6 o'clock direction, is installed in device main body 10; and this wristband 12 allows device main body 10 to be easily put on or taken off from the wrist. Pulse wave detection sensor unit 30 is attached to the base of the index finger and is shielded from light by strap 40. Attaching pulse wave detection sensor unit 30 to the base of a finger in this way keeps cable 20 short and prevents it from getting in the way during running. Furthermore, taking into consideration the temperature distribution between the palm and finger tip in cold weather, the temperature at the finger tip falls substantially, while the temperature at the base of the finger falls relatively little. Therefore, attaching pulse wave detection sensor unit 30 at the base of the finger enables pulse rate (status value) to be accurately measured even during a run outside on a cold day.

Configuration of the Device Main Body:

FIG. 3 is a top view showing the main body of the pulse rate counter of this example, with the wristband and cable removed; FIG. 4 is a side view of this pulse rate counter, obtained from the 3 o'clock direction.

In FIG. 3, device main body 10 is provided with plastic watch case 11 (body case), and the top side of this watch case 11 is provided with liquid crystal display device 13 with an EL backlight for displaying running time, pitch during walking, and pulse wave information such as pulse rate, in addition to current time and date. Liquid crystal display device 13 is provided with first segment display area 131 positioned on the upper left side of the display surface, second segment display area 132 positioned on the upper right side of the display surface, third segment display area 133 positioned on the lower right side of the display surface, and dot display area 134 which can graphically display various types of information positioned on the lower left side of the display.

Control area 5, which performs various types of control and data processing in order to determine the change in pulse rate based on the pulse wave signal (status signal) measured by pulse wave detection sensor unit 30 and to display the result on liquid crystal display device 13, is provided inside watch case 11. Control area 5 is also provided with a timing circuit and thus can display normal time, lap time, split time, etc. on liquid crystal display device 13.

Button switches 111 through 115, which are used for external operations such as time adjustment and display mode switching, are provided on the perimeter of watch case 11. Switch 112 is used to switch between the time mode and the pulse measurement mode. Additionally, larger button switches 116 and 117 are provided on the surface of the watch case. Switch 116 is a lap time switch. Switch 117 is a start/stop for starting and stopping the pulse measurement.

Button-shaped small battery 59 contained inside watch case 11 is installed in pulse rate counter 1, and cable 20 supplies electrical power from battery 59 to pulse wave detection sensor unit 30 and at the same time inputs the detection result of pulse wave detection sensor unit 30 into control area 5 of watch case 11.

Device main body 10 also contains body movement detection sensor device 90 (body movement detection sensor) which uses acceleration sensor 91 to detect body movement as body movement signals.

The size of device main body 10 must be increased as more functions are added to pulse rate counter 1. However, device main body 10 cannot be extended in the 6 or 12 o'clock directions of the watch because it must be worn around a wrist. Therefore, device main body 10 uses watch case 11 which is longer in the 3 and 9o'clock directions than in the 6 and 12 o'clock directions. However, wristband 12 is connected eccentrically toward the 3 o'clockside, leaving extended area 101 in the 9 o'clock direction, viewed from wristband 12, but no such extended area in the 3 o'clock direction. Consequently, this structure, despite the use of long watch case 11, allows free wrist movement and eliminates the possibility of the back of the hand striking watch case 11.

Flat piezoelectric element 58 for a buzzer is positioned in the 9 o'clock direction, viewed from battery 59, inside watch case 11. Because battery 59 is heavier than piezoelectric element 58, the center of gravity of device main body 10 is positioned eccentrically in the 3 o'clock direction. Because wristband 12 is connected to the side on which the center of gravity is located, device main body 10 can be securely attached to the wrist. Furthermore, the positioning of battery 59 and piezoelectric element 58 in the planar direction allows device main body 10 to be thin; battery cover 118 installed on the back side as shown in FIG. 3 allows the user to easily replace battery 59.

Structure for attaching the device main body to the wrist:

In FIG. 4, connecting area 105 for holding stopping pin 121 installed on the end of wristband 12 is formed in the 12 o'clock direction of watch case 11. Receiving area 106 is provided in the 6 o'clock direction of watch case 11, and receiving area 106 is provided with fastener 122 through which wrist band 12 is folded back and which holds in place the middle point of wristband 12 wound around the wrist, in the long direction of the band.

In the 6 o'clock direction of device main body 10, the area from bottom surface 119 to receiving area 106 is formed as an integral part of watch case 11 and forms rotation stop area 108 which is positioned at approximately 115° from bottom surface 119. That is, when wristband 12 is used to attach device main body 10 to top area L1 (side of the back of the hand) of right wrist L (arm), bottom surface 119 of watch case 11 tightly contacts top area L1 of wrist L while rotation stop area 108 contacts side area L2 where radius R is located. In this state, bottom surface 119 of device main body 10 more or less straddles radius R and ulna U, while rotation stop area 108 and the area between bent area 109 of bottom surface 119 and rotation stop area 108 contact radius R. Because rotation stop area 108 and bottom surface 119 form an anatomically ideal angle of approximately 115° as explained above, device main body 10 will not turn around arm L even if an attempt is made to turn it in the direction of arrows A or B. Furthermore, because the rotation of device main body 10 is restricted only in two locations on the side of the arm by bottom surface 119 and rotation stop area 108, bottom surface 119 and rotation stop area 108 securely contact the arm even if it is thin, and provide a secure rotation stopping effect and comfortable fit even if the arm is thick.

Configuration of the Pulse Wave Detection Sensor Unit:

FIG. 5 shows a cross-section of the pulse wave detection sensor unit of this working example.

In this figure, component housing space 300 is formed between the casing of pulse wave detection sensor unit 30 and bottom lid 302 on the bottom side of sensor frame 36. Circuit board 35 is positioned inside component housing space 300. LED 31, phototransistor 32, and other electronic components are mounted on circuit board 35. One end of cable 20 is fastened to pulse wave detection sensor unit 30 by bushing 393, and various wires of cable 20 are soldered to various patterns on circuit board 35. Pulse wave detection sensor unit 30 is attached to the finger such that cable 20 is extended from the base of the finger toward device main body 10. Therefore, LED 31 and phototransistor 32 are arranged along the length of the finger, with LED 31 positioned on the finger tip side and phototransistor 32 positioned at the base of the finger. This configuration provides the effect of making it difficult for the ambient light to reach phototransistor 32.

In pulse wave detection sensor unit 30, a light transmission window is formed by translucent plate 34 which is made of a glass plate on the upper area of sensor frame 36, and the light-emitting surface and light-receiving surface of LED 31 and phototransistor 32, respectively, are oriented toward said translucent plate 34. Because of such a configuration, when a finger surface is pressed onto external surface 341 of translucent plate 34, LED 31 emits light toward the finger surface and phototransistor 32 can receive part of the light emitted by LED 31 that is reflected by the finger. Note that external surface 341 of translucent plate 34 protrudes farther than surrounding area 361 in order to improve its contact with the finger surface.

In this working example, an InGaN (indium-gallium-nitrogen) blue LED is used as LED 31, and its emission spectrum possesses a peak at 450 nm and its emission wavelength ranges from 350 to 600 nm. To match with LED 31 possessing such characteristics, a GaAsP (gallium-arsenic-phosphorus) phototransistor is used as phototransistor 32, and the light-receiving wavelength of the element itself ranges from 300 to 600 nm, with some sensitive areas also at or below 300 nm.

When pulse wave detection sensor unit 30 thus configured is attached to the base of the finger by sensor-fastening strap 40 and light is emitted from LED 31 toward the finger, the light reaches blood vessels, and part of the light is absorbed by hemoglobin in the blood and part of it is reflected. The light reflected by the finger (blood) is received by phototransistor 32, and the change in the amount of received light corresponds to the change in the blood volume (pulse wave in the blood). That is, because the reflected light becomes weak when the blood volume is high and becomes strong when the blood volume is low, data such as pulse rate can be measured by optically detecting the intensity of the reflected light as a pulse wave signal.

This working example uses LED 31 with an emission wavelength range of between 350 and 600 nm and phototransistor 32 with a light-receiving wavelength range of between 300 and 600 nm, and vital information is displayed based on the results taken in the overlapping wavelengths of between approximately 300 and approximately 600 nm, i.e., wavelengths of approximately 700 nm or shorter. When such pulse wave detection sensor unit 30 is used, even if the ambient light strikes the exposed part of the finger, lights with wavelengths of 700 nm or shorter contained in the ambient light do not use the finger as a light guide to reach phototransistor 32 (light-receiving area). The reason for this is as follows. Because lights with wavelengths of 700 nm or shorter contained in the ambient light do not easily penetrate the finger, the ambient light reaching the area of the finger not covered by the sensor fastening strap 40 will not penetrate the finger to reach phototransistor 32. In contrast, if an LED possessing an emission peak at around 880 nm and a silicon phototransistor are used, a light-receiving wavelength range of between 350 and 1,200 nm will result. In such a case, changes in the ambient light level tend to cause measurement errors because pulse waves will be detected using a light with 1 mm wavelength which can use the finger as a light guide to easily reach phototransistor 32.

Furthermore, because pulse wave information is obtained using lights with approximately 700 nm or shorter wavelengths, the S/N ratio of the pulse wave signal based on blood volume change is high. The reason for this is as follows. The absorption coefficient of hemoglobin in the blood for lights with wavelengths of between 300 and 700 nm is several times to approximately one hundred or more times larger than the absorption coefficient for a light with wavelength of 800 nm which has been conventionally used as the detection light. As a result, lights with wavelengths of between 300 and 700 nm change sensitively to blood volume changes, producing higher pulse wave detection rate (S/N ratio) based on blood volume change.

Configuration of the Control Area:

FIG. 6 is a functional block diagram showing the configuration of the pulse rate counter in this example.

In this figure, pulse wave detection sensor unit 30 (pulse wave detection sensor) detects pulse waves from the body, and outputs the detected pulse wave signal (analog signal) to pulse wave signal amplification circuit 402. Body movement detection sensor device 90 detects the movement of the user whose pulse is being measured, and outputs the detected body movement signal (analog signal) to body movement signal amplification circuit 406.

As described above, pulse wave detection sensor unit 30 uses a combination of phototransistor 32 and LED 31. That is, the light from LED 31 is shone onto the body, and the light reflected from the body (or transmitted light) is detected by phototransistor 32. Note that an acceleration sensor is used as body movement detection sensor device 90 (body movement detection sensor).

Pulse wave signal amplification circuit 402 amplifies a pulse wave signal and outputs the result to pulse wave signal A/D converter 403. Pulse wave signal A/D converter 403 converts a pulse wave signal from analog to digital, and outputs the result to pulse wave signal FFT circuit 404 (which corresponds to first calculation means 103 in FIG. 1). Pulse wave signal FFT circuit 404 applies FFT (high-speed Fourier transformation) to the signal output by pulse wave signal A/D converter 403, and outputs the frequency analysis result (which corresponds to the spectrum in FIG. 13A) to pulse wave component extraction means 410.

Meanwhile, body movement signal amplification circuit 406 amplifies a body movement signal and outputs the result to body movement signal A/D converter 407. Body movement signal A/D converter 407 converts a body movement signal from analog to digital, and outputs the result to body movement signal FFT circuit 408 (which corresponds to second calculation means 106 in FIG. 1). Body movement signal FFT circuit 408 applies FFT (high-speed Fourier transformation) to the signal output by body movement signal A/D converter 407, and outputs the frequency analysis result (which corresponds to the spectrum in FIG. 13B) to pulse wave component extraction means 410.

Pulse wave component extraction means 410 extracts the frequency corresponding to the pulse only from the frequency analysis result of pulse wave signal FFT circuit 404, and outputs the result to pulse rate calculation means 411 (the first extraction method). Alternatively, pulse wave component extraction means 410 can compare the frequency analysis result of pulse wave signal FFT circuit 404 with the frequency analysis result of body movement signal FFT circuit 408, subtract the frequency component of the body movement obtained by body movement signal FFT circuit 408 from the frequency component of pulse wave signal FFT circuit 404, and output the extracted result of the frequency corresponding to the pulse rate to pulse rate calculation means 411 (the second extraction method).

Extraction method switching means 409A determines whether the user is resting or exercising based on the signal obtained by body movement signal A/D converter 407, and based on the result, instructs pulse wave component extraction means 410 to use the first or second extraction method. In other words, extraction method switching means 409A instructs pulse wave component extraction means 410 to use the first extraction method which extracts the frequency corresponding to the pulse from the frequency component of the pulse obtained by pulse wave signal FFT circuit 404, if it is determined that the user is resting. Conversely, extraction method switching means 409A instructs pulse wave component extraction means 410 to use the second extraction method which extracts the frequency corresponding to the pulse by subtracting the frequency component of the body movement obtained by body movement signal FFT circuit 408 from the frequency component of the pulse obtained by pulse wave signal FFT circuit 404, if it is determined that the user is exercising.

Pulse rate calculation means 411 converts the frequency obtained by pulse wave component extraction means 410 to a pulse rate, and outputs it to display area 412. Display area 412 displays the pulse rate obtained by pulse rate calculation means 411 on liquid crystal display device 13.

In this example, pulse wave component extraction means 410, extraction method switching means 409A, and pulse rate calculation means 411 all include microcomputers that run according to pre-stored programs.

Signal Processing Detail:

FIGS. 7A and 7B are a flow chart showing the sequence in which body movement signal frequency is first obtained, the extraction method is determined, and then pulse wave is obtained.

In FIGS. 6, 7A, and 7B pulse wave component extraction means 410 identifies the tallest body movement spectrum in the output signal of body movement signal FFT circuit 408 as the body movement frequency component (step S601).

Extraction method switching means 409A extracts the largest from the group of data that were obtained by body movement signal A/D converter 407 and that are to be processed by FFT circuit 408 (step S602). The extraction method to be used by pulse wave component extraction means 410 is determined based on whether the extracted value is equal to or greater than, or smaller than constant A1 (step S603). Here, constant A1 is an important threshold value that controls the operation of pulse wave component extraction means 410, and becomes the reference for determining whether the user is exercising or resting.

In step S603, if the extracted value is equal to or greater than constant A1 (indicating that the user is exercising), the pulse wave component is extracted by the second extraction method according to the procedure described below. First, assuming that the body movement frequency component identified in step S601 is fin, whether or not any body movement component that is equal to or greater than constant TH exists in ½ frequency of fin is checked (step S604). If a body movement component that is equal to or greater than constant TH exists, fin is identified as the second harmonic (step S605). If none exists, whether or not any body movement component that is equal to or greater than constant TH exists in ⅓ frequency of fin is checked (step S606). If a body movement component that is equal to or greater than constant TH exists, fm is identified as the third harmonic (step S607). If none exits, fin is identified as the fundamental harmonic (step S608).

These steps determine the order (specified by variable HMC) of the identified fm in terms of harmonic, and determine the numerical value (variable HMC) with which to divide fm in order to obtain the fundamental harmonic in step S609. In step S609, the fundamental harmonic of the body movement is obtained.

In the succeeding steps S610 through S613, frequency and body movement frequency are compared in the order of size beginning with the line spectrum possessing the largest pulse wave frequency analysis result, in order to determine whether the frequency matches the fundamental harmonic, the second harmonic, or the third harmonic (steps S610, S611, S612, and S613). In other words, these steps determine whether or not any overlapping frequency exists between the frequency analysis result of the pulse wave signal detected by pulse wave detection sensor unit 30 and the frequency analysis result of the body movement signal detected by body movement detection sensor device 90.

The frequency component of the pulse wave is first compared to the fundamental harmonic of the body movement frequency in step S611, next to the second harmonic of the body movement frequency in step S612, and then to the third harmonic of the body movement frequency in step S613. This comparison is repeated for all detected frequency components of the pulse wave, and if a matching frequency exists, that frequency component is removed. Note that it is acceptable to use only the frequency component of the pulse wave, possessing the highest level, for determination. This is because the level of the fundamental harmonic of a pulse wave is usually the highest. Through these steps, the largest pulse wave frequency component fn which does not match any body movement component can be extracted in step S614.

On the other hand, in step S603, if the largest value resulting from the A/D conversion of the body movement signal is smaller than constant A1 (indicating that the user is resting), the largest pulse wave frequency component among the pulse wave spectrum of the signal that is output by pulse wave signal FFT circuit 404 is considered to be fn (step S615). The extraction method described above is the first extraction method to be performed by pulse wave component extraction means 410 when the user is resting.

Main Effects of Working Example 1:

As explained above, extraction method switching means 409A automatically determines whether or not the user is resting or exercising based on the amplitude level of the body movement signal, and based on this result, automatically switches to the pulse wave component extraction method that should be used by pulse wave component extraction means 410. As a result, the processing in step S615 (the first extraction method) occurs as long as the largest value resulting from the A/D conversion of the body movement signal is judged to be smaller than constant A1 in step S603, even if a frequency component of noise appears in the frequency analysis result of body movement signal FFT circuit 408 and the frequency component of the noise happens to match the pulse wave frequency component. Therefore, pulse rate counter 1 of this example enables accurate pulse rate measurement free from the effect of noise of body movement signals, regardless of whether the user is resting or exercising.

In this example, the user's state (exercising or resting) is judged by determining whether the largest from the group of data that were obtained by body movement signal A/D converter 407 is equal to or greater than, or smaller than constant A1; and such a threshold normally varies among different users (subjects), or even for the same user (subject) depending on the exercising condition. Therefore, this value A1 is best determined empirically. For example, in body movement detection sensor device 90, the relationship between the exercising condition (acceleration G) of the user and the output of acceleration sensor 91 is nearly linear as shown in FIG. 8, and acceleration 1G corresponds to 8 mV in terms of the output from acceleration sensor 91. Therefore, when the acceleration level (horizontal axis) is divided into rest, very light exercise, and exercise periods in FIG. 8, output voltage that clearly differentiates between very light exercise and exercise periods is selected as A1. That is, by setting threshold A1 at 7.2 mV in this measurement example, the user can be accurately judged to be exercising if the output of acceleration sensor 91 is at least 7.2 mV, and resting if the output of acceleration sensor 91 is less than 7.2 mV.

Note that threshold A1 can be set as a unique value for each pulse rate counter, or the pulse rate counter can be configured such that A1 can be set by the user.

WORKING EXAMPLE 2:

FIG. 9 is a functional block diagram showing the configuration of the pulse rate counter of this example. Since the basic structure of this pulse rate counter is the same as that of the pulse rate counter in Working example 1, the explanation of the structure of the device main body will be omitted, and only its control area will be explained. Even for the control area, the same symbols are used to represent areas that are the same as in Working example 1, with detailed explanations omitted.

As can be seen from FIG. 9, the pulse rate counter of this example also comprises pulse wave detection sensor unit 30, pulse wave signal amplification circuit 402, pulse wave signal A/D converter 403, pulse wave signal FFT circuit 404, body movement detection sensor device 90, body movement signal amplification circuit 406, body movement signal A/D converter 407, body movement signal FFT circuit 408, pulse rate calculation means 411, and display area 412; and their elements are the same as in the pulse rate counter in Working example 1 described above.

In this example also, pulse wave component extraction means 410 extracts the frequency corresponding to the pulse from the frequency analysis result (which corresponds to spectrum (a) in FIG. 13) of pulse wave signal FFT circuit 404, and outputs the result to pulse rate calculation means 411 (the first extraction method). Alternatively, pulse wave component extraction means 410 can compare the frequency analysis results of pulse wave signal FFT circuit 404 with the frequency analysis result of body movement signal FFT circuit 408 (which corresponds to spectrum (b), in FIG. 13), subtract the frequency component of the body movement obtained by body movement signal FFT circuit 408 from the frequency component of pulse wave signal FFT circuit 404, and output the extracted result of the frequency corresponding to the pulse rate to pulse rate calculation means 411 (the second extraction method).

In this example, extraction method switching means 409B determines whether the user is resting or exercising based on the base line spectrum of the frequency analysis result (spectrum) of the body movement signal obtained by body movement signal FFT circuit 408, and based on the result, instructs pulse wave component extraction means 410 to use the first or second extraction method. In other words, extraction method switching means 409B instructs pulse wave component extraction means 410 to use the first extraction method which extracts the frequency corresponding to the pulse from the frequency component of the pulse obtained by pulse wave signal FFT circuit 404, if it is determined that the user is resting. Conversely, extraction method switching means 409B instructs pulse wave component extraction means 410 to use the second extraction method which extracts the frequency corresponding to the pulse by subtracting the frequency component of the body movement obtained by body movement signal FFT circuit 408 from the frequency component of the pulse obtained by pulse wave signal FFT circuit 404, if it is determined that the user is exercising.

FIGS. 10A and 10B are a flow chart showing the sequence in which body movement signal frequency and the power (level) of the base line spectrum are first obtained, the extraction method is determined, and then pulse wave is obtained.

In FIGS. 9, 10A and 10B, pulse wave component extraction means 410 identifies the tallest body movement spectrum in the frequency analysis result of body movement signal FFT circuit 408 as the body movement frequency component (step S701).

Extraction method switching means 409B determines the power of the base line spectrum of the body movement frequency component (step S702). Then, the extraction method is switched based on whether the power of this base line spectrum is equal to or greater than, or smaller than constant A2 (step S703). Here, constant A2 can be determined empirically as constant A1 was in Working example 1.

In step S703, if the power of the base line spectrum is equal to or greater than constant A2 (indicating that the user is exercising), the pulse wave component is extracted by the second extraction method according to the procedure described below. First, assuming that the body movement frequency component identified in step S701 is fm, whether or not any body movement component that is equal to or greater than constant TH exists in ½ frequency of fm is checked (step S704). If a body movement component that is equal to or greater than constant TH exists, fm is identified as the second harmonic (step S705). If none exists, whether or not any body movement component that is equal to or greater than constant TH exists in ⅓ frequency of fm is checked (step S706). If a body movement component that is equal to or greater than constant TH exists, fin is identified as the third harmonic (step S707). If none exits, fin is identified as the fundamental harmonic (step S708).

These steps determine the order (specified by variable HMC) of the identified fin in terms of harmonic, and determine the numerical value (variable HMC) with which to divide fin in order to obtain the fundamental harmonic in step S709. In step S709, the fundamental harmonic of the body movement is obtained.

In the succeeding steps S710 through S713, frequency and body movement frequency are compared in the order of size beginning with the line spectrum possessing the largest pulse wave frequency analysis result, in order to determine whether the frequency matches the fundamental harmonic, the second harmonic, or the third harmonic (steps S710, S711, S712, and S713). Through these steps, the largest pulse wave frequency component fn which does not match any body movement component can be extracted in step S714.

On the other hand, in step S703, if the power of the base line spectrum is smaller than constant A2 (indicating that the user is resting), the largest pulse wave frequency component among the pulse wave spectrum of the signal that is output by pulse wave signal FFT circuit 404 is considered to be fn (step S715). The extraction method described above is the first extraction method to be performed by pulse wave component extraction means 410 when the user is resting.

As explained above, extraction method switching means 409B automatically determines whether or not the user is resting or exercising based on the level (power) of the tallest spectrum among the frequency spectrums of the body movement signal, and based on this result, automatically switches to the pulse wave component extraction method that should be used by pulse wave component extraction means 410. As a result, the processing in step S715 (the first extraction method) occurs as long as the power of the base line spectrum of the frequency component of noise is judged to be smaller than constant A2 set in step S703, even if a frequency component of noise appears in the frequency analysis result of body movement signal FFT circuit 408 and the frequency component of the noise happens to match the pulse wave frequency component. Therefore, pulse rate counter 1 of this example enables accurate pulse rate measurement free from the effect of noise of body movement signals, regardless of whether the user is resting or exercising.

WORKING EXAMPLE 3:

Since the basic structure of the pulse rate counter in this example is the same as that of the pulse rate counter in Working example 1, the explanation of the structure of the device main body will be omitted. Furthermore, since the basic configuration of the control area is the same as that of the pulse rate counter in Working example 2, only a brief explanation will be provided, with reference to FIG. 9.

In FIG. 9, the control area of the pulse rate counter of this example also comprises pulse wave detection sensor unit 30, pulse wave signal amplification circuit 402, pulse wave signal A/D converter 403, pulse wave signal FFT circuit 404, body movement detection sensor device 90, body movement signal amplification circuit 406, body movement signal A/D converter 407, body movement signal FFT circuit 408, pulse rate calculation means 411, and display area 412; and their elements are the same as in the pulse rate counter in Working examples 1 and 2 described above.

However, in this example, extraction method switching means 409C determines whether the user is resting or exercising based on the degree of variation in the levels of the multiple frequency spectrums obtained by body movement signal FFT circuit 408, and based on the result, instructs pulse wave component extraction means 410 to use the first or second extraction method. In other words, extraction method switching means 409C instructs pulse wave component extraction means 410 to use the first extraction method which extracts the frequency corresponding to the pulse from the frequency component of the pulse obtained by pulse wave signal FFT circuit 404, if it is determined that the user is resting. Conversely, extraction method switching means 409C instructs pulse wave component extraction means 410 to use the second extraction method which extracts the frequency corresponding to the pulse by subtracting the frequency component of the body movement obtained by body movement signal FFT circuit 408 from the frequency component of the pulse obtained by pulse wave signal FFT circuit 404, if it is determined that the user is exercising.

The above process will be explained with reference to FIGS. 11A and 11B. FIGS. 11A and 11B are a flow chart showing the sequence in which body movement signal frequency and the power (level) of the base line spectrum are first obtained, the extraction method is determined, and then pulse wave is obtained.

In FIGS. 9, 11A and 11B pulse wave component extraction means 410 identifies the tallest body movement spectrum among the output signals of body movement signal FFT circuit 408 as the body movement frequency component (step S801). Extraction method switching means 409C determines power P1 of the base line spectrum of the body movement frequency component obtained (step S802).

Next, P2, the sum total of the power of all base line spectrums, excluding the frequency of the largest base line spectrum, is determined based on the FFT processing result of the body movement signal (step S803). Value B is then determined using the equation (B=P1/P2) (step S804). Here, B indicates the ratio (relative comparison result) between the power of the largest body movement frequency component and P2, the summation of the power of all base line spectrums, excluding the frequency of the largest base line spectrum. In other words, when a distinct body movement is present (during exercise), power P1 of the largest base line spectrum increases, resulting in a larger value B. Conversely, when the body movement is small (during rest), power P1 of the largest base line spectrum becomes nearly equal to the power of all base line spectrums, excluding the frequency of the largest base line spectrum, resulting in a smaller value B. Therefore, value B determined here is large when body movement frequency appears in body movement signal FFT circuit 408, and is small when only noise components are present.

Next, the extraction method is selected depending on whether or not value B determined in step S804 is equal to or greater than constant A3, or smaller than A3 (step S805).

In step S805, if value B is equal to or greater than constant A3 (indicating that the user is exercising), the pulse wave component is extracted by the second extraction method according to the procedure described below. First, assuming that the body movement frequency component identified in step S803 is fm, whether or not any body movement component that is equal to or greater than constant TH exists in ½ frequency of fm is checked (step S806). If a body movement component that is equal to or greater than constant TH exists, fm is identified as the second harmonic (step S807). If none exists, whether or not any body movement component that is equal to or greater than constant TH exists in ⅓ frequency of fm is checked (step S808). If a body movement component that is equal to or greater than constant TH exists, fin is identified as the third harmonic (step S809). If none exits, fm is identified as the fundamental harmonic (step S810).

These steps determine the order (specified by variable HMC) of the identified fin in terms of harmonic, and determine the numerical value (variable HMC) with which to divide fin in order to obtain the fundamental harmonic in step S811. In step S811, the fundamental harmonic of the body movement is obtained.

In the succeeding steps S812 through S815, frequency of line spectrum is compared to body movement frequency in the order of size beginning with the line spectrum possessing the largest pulse wave frequency analysis result, in order to determine whether the frequency matches the fundamental harmonic, the second harmonic, or the third harmonic (steps S812, S813, S814, and S815). Through these steps, the largest pulse wave frequency component fn which does not match any body movement component can be extracted in step S816.

On the other hand, in step S805, if the power of the base line spectrum of the body movement frequency component is smaller than constant A3, the largest pulse wave frequency component among the pulse wave spectrum of the signal that is output by pulse wave signal FFT circuit 404 is considered to be fn (step S817). The extraction method described above is the first extraction method to be performed by pulse wave component extraction means 410 when the user is resting.

As explained above, extraction method switching means 409C automatically determines whether or not the user is resting or exercising based on the degree of variation in the level (power) of spectrum among the frequency spectrums of the body movement signal, and based on this result, automatically switches to the pulse wave component extraction method that should be used by pulse wave component extraction means 410. As a result, the processing in step S817 (the first extraction method) occurs as long as the power of the base line spectrum of the frequency component of noise is judged to be smaller than constant A3 set in step S805, even if a frequency component of noise appears in the frequency analysis result of body movement signal FFT circuit 408 and the frequency component of the noise happens to match the pulse wave frequency component. Therefore, pulse rate counter 1 of this example enables accurate pulse rate measurement free from the effect of noise of body movement signals, regardless of whether the user is resting or exercising.

As explained above, in the pulse rate counter of the invention, the extraction method switching means automatically determines whether the user is resting or exercising based on the body movement signal, and based on this results, automatically selects an appropriate pulse wave component extraction method to be used by the pulse wave component extraction means. Therefore, the pulse rate counter of this invention enables accurate pulse rate measurement free from the effect of noise of body movement signals, regardless of whether the user is resting or exercising.

While the invention has been described in conjunction with several specific embodiments, it is evident to those skilled in the art that many further alternatives, modifications and variations will be apparent in light of the foregoing description. Thus, the invention described herein is intended to embrace all such alternatives, modifications, applications and variations as may fall within the spirit and scope of the appended claims.

What is claimed is:

1. A pulse rate counter, comprising:

first calculation means responsive to a pulse wave signal of a body for analyzing the frequency of the pulse wave signal and for outputting a pulse wave frequency analysis result;

second calculation means responsive to a body movement signal of the body for analyzing the frequency of the body movement signal and for outputting a body movement frequency analysis result;

pulse wave component extraction means operating in one of a first and a second extraction method for extracting pulse frequency components from the frequency analysis results output by the first and second calculation means;

extraction method switching means responsive to the body movement signal for determining an amplitude level of the body movement signal and for switching the pulse wave component extraction means to operate in one of the first and second methods according to the amplitude level of the body movement signal; and pulse rate calculation means for converting the pulse frequency components extracted by the pulse wave component extraction means to a pulse rate.

2. The pulse rate counter of claim 1, further comprising:

pulse wave detection means for detecting the pulse wave signal of the body and being coupled to the first calculation means;

and body movement detection means for detecting the body movement signal of the body and being coupled to the second calculation means.

3. The pulse rate counter of claim 1, further comprising display means coupled to the pulse rate calculation means for displaying the pulse rate converted by the pulse rate calculation means.

4. The pulse rate counter of claim 1, wherein the pulse wave component extraction means comprises a first extraction means operating in the first method for extracting pulse frequency components based on the frequency analysis result of the first calculation means, and a second extraction means operating in the second method for extracting pulse frequency components based on the frequency analysis results of both the first and second calculation means.

5. A pulse rate counter, comprising:

first calculation means for analyzing the frequency of a pulse wave signal of a body and outputting frequency analysis result;

second calculation means for analyzing the frequency of a body movement signal of the body and outputting frequency analysis result;

pulse wave component extraction means for extracting pulse frequency components from the frequency analysis results output by the first and second calculation means;

extraction method switching means for switching the pulse wave component extraction means to operate in a predetermined method according to the frequency spectrum level of the frequency analysis result output by the second calculation means; and pulse rate calculation means for converting the pulse frequency components extracted by the pulse wave component extraction means to a pulse rate for display.

6. The pulse rate counter of claim 5, further comprising:

pulse wave detection means for detecting the pulse wave signal of the body; and body movement detection means for detecting the body movement signal of the body.

7. The pulse rate counter of claim 5, further comprising display means for displaying the pulse rate converted by the pulse rate calculation means.

8. The pulse rate counter of claim 5, wherein the pulse wave component extraction means is operable in two extraction methods comprising a first extraction method for extracting pulse frequency components based on the frequency analysis result of the first calculation means, and a second extraction method for extracting pulse frequency components based on the frequency analysis results of both the first and second calculation means.

9. A pulse rate counter, comprising:

first calculation means for analyzing the frequency of a pulse wave signal of a body and outputting frequency analysis result;

second calculation means for analyzing the frequency of a body movement signal of the body and outputting frequency analysis result;

pulse wave component extraction means for extracting pulse frequency components from the frequency analysis results output by the first and second calculation means;

extraction method switching means for switching the pulse wave component extraction means to operate in a predetermined method according to the degree of variation in the levels of multiple frequency spectrums of the frequency analysis result output by the second calculation means; and pulse rate calculation means for converting the pulse frequency components extracted by the pulse wave component extraction means to a pulse rate for display.

10. The pulse rate counter of claim 9, wherein the pulse wave component extraction means is operable in two extraction methods comprising a first extraction method for extracting pulse frequency components based on the frequency analysis result of the first calculation means, and a second extraction method for extracting pulse frequency components based on the frequency analysis results of both the first and second calculation means.

11. A wrist-mountable electronic device, comprising:

a main case; and a pulse rate counter disposed in the main case and comprising:

pulse wave detection means for detecting a pulse wave signal of a body;

body movement detection means for detecting a body movement signal of the body;

first calculation means coupled to the pulse wave detection means for analyzing the frequency of the pulse wave signal and for outputting a pulse wave frequency analysis result;

second calculation means coupled to the body movement detection means for analyzing the frequency of the body movement signal and for outputting a body movement frequency analysis result;

pulse wave component extraction means operating in one of a first and a second extraction method for extracting pulse frequency components from the frequency analysis results output by the first and second calculation means;

extraction method switching means responsive to the body movement signal for determining an amplitude level of the body movement signal and for switching the pulse wave component extraction means to operate in one of the first and second methods according to the amplitude level of the body movement signal; and pulse rate calculation means for converting the pulse frequency components extracted by the pulse wave component extraction means to a pulse rate; and display means for displaying the pulse rate converted by the pulse rate calculation means.

12. The electronic device of claims 11 wherein the pulse wave component extraction means comprises a first extraction means operating in the first method for extracting pulse frequency components based on the frequency analysis result of the first calculation means, and a second extraction means operating in the second method for extracting pulse frequency components based on the frequency analysis results of both the first and second calculation means.

13. A wrist-mountable electronic device, comprising:

a main case; and a pulse rate counter disposed in the main case and comprising:

pulse wave detection means for detecting a pulse wave signal of a body;

body movement detection means for detecting a body movement signal of the body;

first calculation means for analyzing the frequency of the pulse wave signal of the body and outputting frequency analysis result;

second calculation means for analyzing the frequency of the body movement signal of the body and outputting frequency analysis result;

pulse wave component extraction means for extracting pulse frequency components from the frequency analysis results output by the first and second calculation means;

extraction method switching means for switching the pulse wave component extraction means to operate in a predetermined method according to the frequency spectrum level of the frequency analysis result output by the second calculation means; and pulse rate calculation means for converting the pulse frequency components extracted by the pulse wave component extraction means to a pulse rate; and display means for displaying the pulse rate converted by the pulse rate calculation means.

14. The electronic device of claims 13 wherein the pulse wave component extraction means is operable in two extraction methods comprising a first extraction method for extracting pulse frequency components based on the frequency analysis result of the first calculation means, and a second extraction method for extracting pulse frequency components based on the frequency analysis results of both the first and second calculation means.

15. A wrist-mountable electronic device, comprising:

a main case; and a pulse rate counter disposed in the main case and comprising:

pulse wave detection means for detecting a pulse wave signal of a body;

body movement detection means for detecting a body movement signal of the body;

first calculation means for analyzing the frequency of the pulse wave signal of the body and outputting frequency analysis result;

second calculation means for analyzing the frequency of the body movement signal of the body and outputting frequency analysis result;

pulse wave component extraction means for extracting pulse frequency components from the frequency analysis results output by the first and second calculation means;

extraction method switching means for switching the pulse wave component extraction means to operate in a predetermined method according to the degree of variation in the levels of multiple frequency spectrums of the frequency analysis result output by the second calculation means; and pulse rate calculation means for converting the pulse frequency components extracted by the pulse wave component extraction means to a pulse rate; and display means for displaying the pulse rate converted by the pulse rate calculation means.

16. The electronic device of claims 15 wherein the pulse wave component extraction means is operable in two extraction methods comprising a first extraction method for extracting pulse frequency components based on the frequency analysis result of the first calculation means, and a second extraction method for extracting pulse frequency components based on the frequency analysis results of both the first and second calculation means.

17. A method of measuring a pulse rate of a body, comprising:

detecting a pulse wave signal of the body;

detecting a body movement signal of the body;

analyzing the frequency of the pulse wave signal of the body to produce a first frequency analysis result;

analyzing the frequency of the body movement signal of the body to produce a second frequency analysis result;

determining an amplitude level of the body movement signal, extracting pulse frequency components from the first and second frequency analysis results in one of a first and a second method according to the amplitude level of the body movement signal; converting the extracted pulse frequency to a pulse rate; and displaying the converted pulse rate.

18. A method of measuring a pulse rate of a body, comprising:

detecting a pulse wave signal of the body;

detecting a body movement signal of the body;

analyzing the frequency of the pulse wave signal of the body to produce a first frequency analysis result;

analyzing the frequency of the body movement signal of the body to produce a second frequency analysis result;

extracting pulse frequency components from the first and second frequency analysis results according to the frequency spectrum level of the second frequency analysis result; and converting the extracted pulse frequency components to a pulse rate; and displaying the pulse rate converted by the pulse rate calculation means.

19. A method of measuring a pulse rate, comprising:

detecting a pulse wave signal of the body;

detecting a body movement signal of the body;

analyzing the frequency of the pulse wave signal of the body to produce a first frequency analysis result;

analyzing the frequency of the body movement signal of the body to produce a second frequency analysis result;

extracting pulse frequency components from the first and second frequency analysis results according to the degree of variation in the levels of multiple frequency spectrums of the second frequency analysis result; and converting the extracted pulse frequency components to a pulse rate; and displaying the pulse rate converted by the pulse rate calculation means.

* * * * *

UNITED STATES PATENT AND TRADEMARK OFFICE
CERTIFICATE OF CORRECTION

PATENT NO. : 5,776,070
DATED : Jul. 7, 1998
INVENTOR(S) : Kitazawa et al.

It is certified that error appears in the above-identified patent and that said Letters Patent is hereby corrected as shown below:

On the title page item [54], and in col. 1, line 2, "AMPTITUDE" should read -- AMPLITUDE --.

Column 18, line 19, change "claims" to --claim--.

line 58, change "claims" to --claim--.

Column 19, line 29, change "claims" to --claim--.

Column 20, line 2, change "signal," to --signal;--.

Signed and Sealed this

Twenty-seventh Day of July, 1999

Attest:

Q. TODD DICKINSON

*Attesting Officer*   *Acting Commissioner of Patents and Trademarks*

UNITED STATES PATENT AND TRADEMARK OFFICE
CERTIFICATE OF CORRECTION

PATENT NO.   : 5,776,070
DATED        : July 7, 1998
INVENTOR(S)  : Kouji Kitazawa et al.

It is certified that error appears in the above-identified patent and that said Letters Patent is hereby corrected as shown below:

<u>Title page,</u>
Item [73], Assignee, insert -- and Seiko Instruments, Inc., Chiba both of -- after "Tokyo,".

Signed and Sealed this

Sixth Day of January, 2004

JAMES E. ROGAN
*Director of the United States Patent and Trademark Office*